(12) United States Patent
Kucklick

(10) Patent No.: US 10,004,393 B2
(45) Date of Patent: Jun. 26, 2018

(54) ARTHROSCOPIC SYSTEM

(71) Applicant: Cannuflow, Inc., Campbell, CA (US)

(72) Inventor: Theodore R. Kucklick, Campbell, CA (US)

(73) Assignee: Cannuflow, Inc., Campbell, CA (US)

( * ) Notice: Subject to any disclaimer, the term of this patent is extended or adjusted under 35 U.S.C. 154(b) by 0 days. days.

(21) Appl. No.: 15/193,609

(22) Filed: Jun. 27, 2016

(65) Prior Publication Data

US 2016/0302656 A1 Oct. 20, 2016

Related U.S. Application Data

(63) Continuation of application No. 12/846,747, filed on Jul. 29, 2010, now Pat. No. 9,375,139.

(51) Int. Cl.
| | |
|---|---|
| *A61B 1/00* | (2006.01) |
| *A61B 1/317* | (2006.01) |
| *A61B 1/05* | (2006.01) |
| *A61B 1/005* | (2006.01) |
| *A61B 1/015* | (2006.01) |

(52) U.S. Cl.
CPC .......... *A61B 1/317* (2013.01); *A61B 1/00045* (2013.01); *A61B 1/0051* (2013.01); *A61B 1/0053* (2013.01); *A61B 1/00096* (2013.01); *A61B 1/00135* (2013.01); *A61B 1/00163* (2013.01); *A61B 1/00177* (2013.01); *A61B 1/00179* (2013.01); *A61B 1/00183* (2013.01); *A61B 1/015* (2013.01); *A61B 1/05* (2013.01)

(58) Field of Classification Search
CPC ............ A61B 1/00064; A61B 1/00071; A61B 1/00091; A61B 1/00094; A61B 1/00096; A61B 1/00135; A61B 1/00142; A61B 1/00183; A61B 1/012; A61B 1/015; A61B 1/05; A61B 1/051; A61B 1/12; A61B 1/126; A61B 1/127; A61B 1/317; A61B 1/303; A61B 1/307; A61B 1/31
USPC ..... 600/105, 121–125, 156–159; 604/23, 26, 604/43–45
See application file for complete search history.

(56) References Cited

U.S. PATENT DOCUMENTS

| | | | | |
|---|---|---|---|---|
| 4,742,817 A | * | 5/1988 | Kawashima | A61B 1/0052 600/104 |
| 5,575,756 A | * | 11/1996 | Karasawa | A61B 1/00068 600/121 |
| 6,379,347 B1 | * | 4/2002 | Maki | A61B 18/24 606/17 |
| 6,562,029 B2 | * | 5/2003 | Maki | A61B 18/24 128/898 |
| 6,626,828 B2 | * | 9/2003 | Dohi | A61B 1/00183 600/171 |
| 6,916,286 B2 | * | 7/2005 | Kazakevich | A61B 1/00105 600/129 |
| 7,553,278 B2 | * | 6/2009 | Kucklick | A61B 1/00135 600/175 |
| 2003/0032863 A1 | * | 2/2003 | Kazakevich | A61B 1/00105 600/173 |
| 2004/0236183 A1 | * | 11/2004 | Durell | A61B 1/00165 600/173 |
| 2006/0276692 A1 | * | 12/2006 | Kucklick | A61B 1/00135 600/175 |

(Continued)

*Primary Examiner* — Ryan Henderson
(74) *Attorney, Agent, or Firm* — K. David Crockett, Esq.; Niky Economy Syrengelas, Esq.; Crockett & Crockett, PC

(57) ABSTRACT

An arthroscope having an elongated core with a square radial cross section.

4 Claims, 13 Drawing Sheets

(56) References Cited

U.S. PATENT DOCUMENTS

| | | | |
|---|---|---|---|
| 2007/0049800 A1* | 3/2007 | Boulais | A61B 1/00103 600/142 |
| 2007/0249907 A1* | 10/2007 | Boulais | A61B 1/0008 600/179 |
| 2009/0012362 A1* | 1/2009 | Kucklick | A61B 1/317 600/121 |
| 2009/0082628 A1* | 3/2009 | Kucklick | A61M 1/0084 600/121 |
| 2009/0187072 A1* | 7/2009 | Manohara | A61B 1/00039 600/109 |
| 2009/0198258 A1* | 8/2009 | Workman | A61B 17/3421 606/148 |
| 2009/0240109 A1* | 9/2009 | Ostrovsky | A61B 1/00071 600/112 |

\* cited by examiner

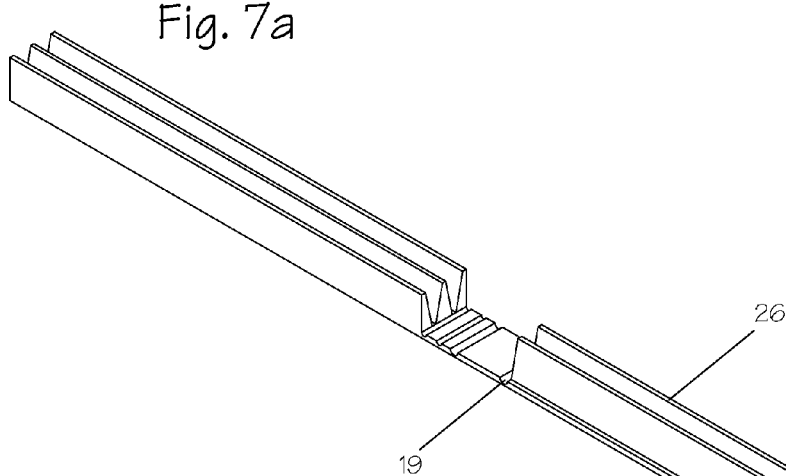
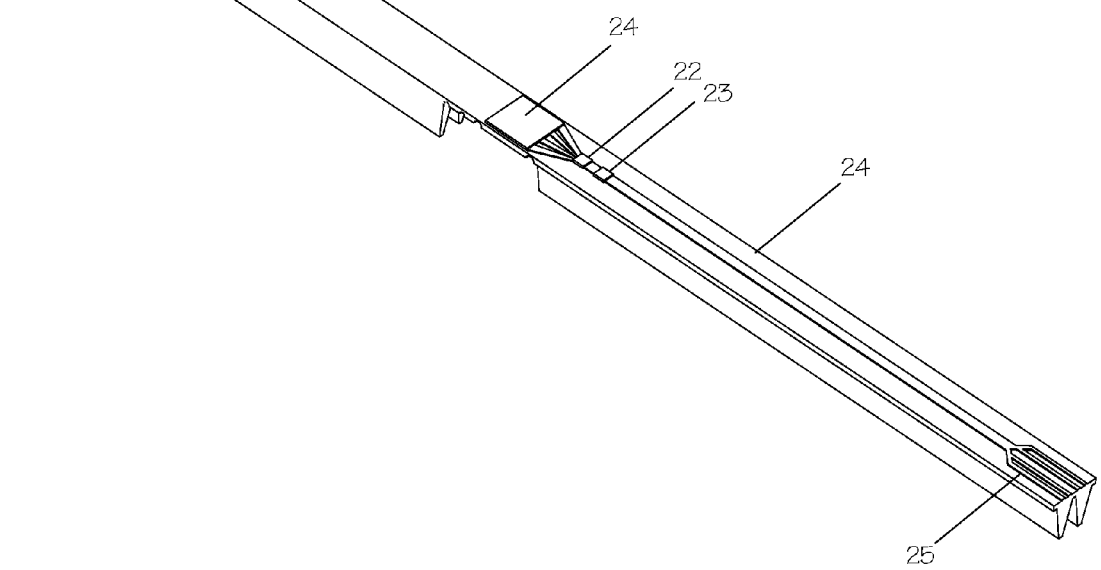

ARTHROSCOPIC SYSTEM

This application is a continuation of U.S. application Ser. No. 12/846,747 filed Jul. 29, 2010, now U.S. Pat. No. 9,375,139

FIELD OF THE INVENTIONS

The inventions described below relate to the field of arthroscopic surgical instruments.

BACKGROUND OF THE INVENTIONS

Arthroscopic surgery involves using optical instruments, such as an arthroscope, to visualize an operating field inside or near a joint of a patient. The same instrument or other instruments may be used to perform a surgical procedure in the operating field.

Known inflow and outflow arthroscope systems generally consist of several elements, which include a flexible or rigid tube, a light that illuminates the area the doctor wants to examine (where the light is typically outside of the body and delivered via an optical fiber system), a lens system that transmits an image to the viewer from the arthroscope and another channel that allows the entry of medical instruments or manipulators. The lens systems typically use pre-manufactured square or rectangular shaped CCD chips. Traditionally, arthroscopes are circular so that the arthroscope does not have sharp edges that may cause trauma to tissue. When the chips are housed within the arthroscope, this results in a great amount of wasted space between the square chips and the circular arthroscope that houses the chips.

SUMMARY

The devices and methods described below provide for an arthroscope having square or rectangular lateral cross section herein after referred to as a rectangle or rectangular. The arthroscope can be used in an arthroscopic system that also includes a scope sheath that is matched to the dimensions of the arthroscope. The system includes a flow system, which sends fluid out of the end of the endoscope and brings debris and other fluid behind the field of view, thus allowing the surgeon to have a clear field of view while using the system.

This architecture allows the arthroscope to have a low profile thus making it less traumatic once introduced into anatomic spaces. Further, configuring the arthroscopic cross-section into the shape of the pre-manufactured CCD chip image configurations reduces costs associated with the manufacture of the scope.

BRIEF DESCRIPTION OF THE DRAWINGS

FIGS. 7a and 7b illustrate another elongated core before it is folded into its final configuration;

DETAILED DESCRIPTION OF THE INVENTIONS

Figure 1:
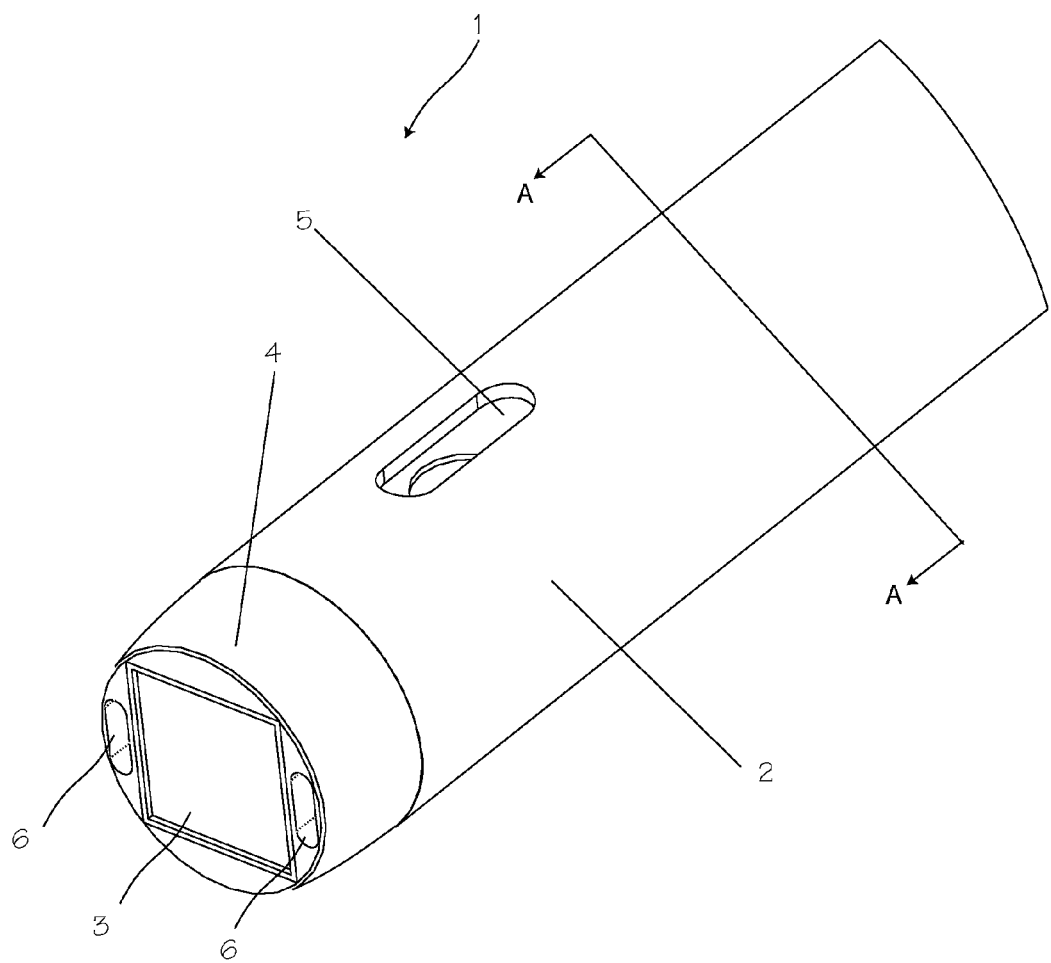
FIG. 1 shows an arthroscope having a sheath that encloses an elongated core that has a square radial cross section; the elongated core has an imaging element on the distal end.
Figure 2:
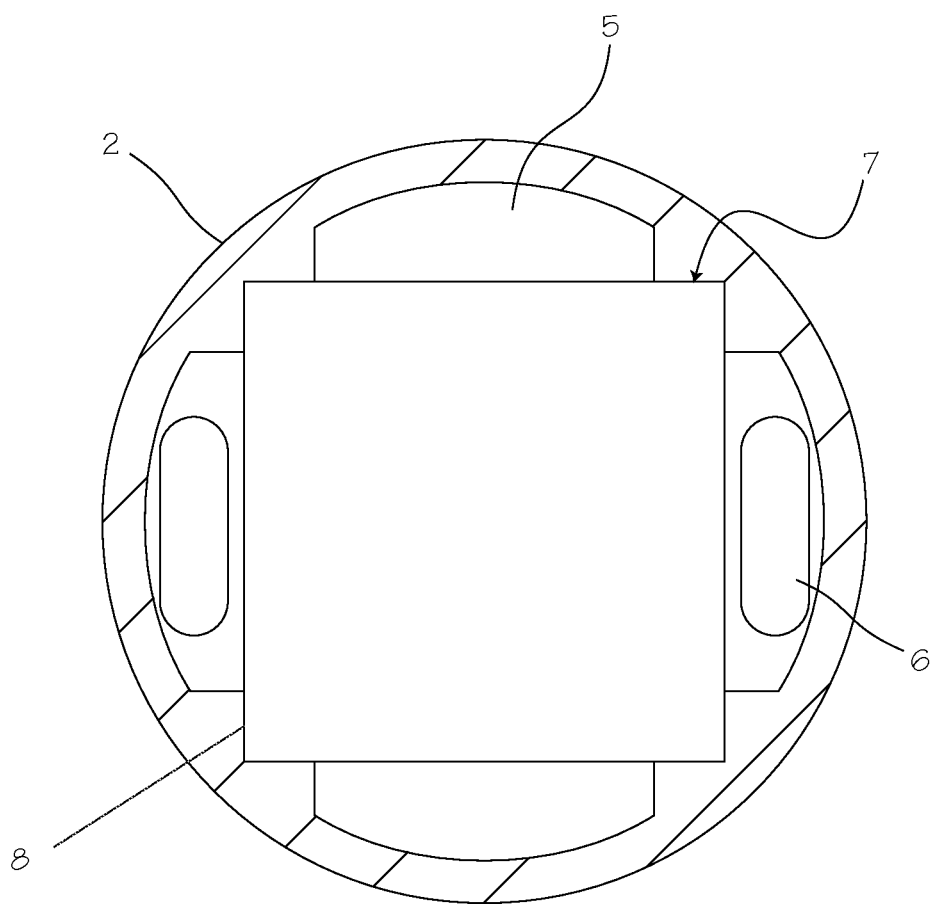
FIG. 2 illustrates a cross-sectional view along Line A-A of FIG. 1.

FIG. 1 shows an arthroscope 1 having a sheath that encloses an elongated core having a square radial cross section (see FIG. 2). Contained centrally within a sheath 2, the elongated core has a square imaging chip 3 located at the distal end of the elongated core. The elongated core and the imaging chip together form the imaging core of the arthroscope. An atraumatic tip 4 at the distal end may also encase the imaging chip. The elongated core has a square radial cross section that allows for the largest possible rectangular chip image package to be used in combination with the smallest possible round fluid sheath outside diameter. This combination allows a clear pocket flow system, which sends fluid out of the end of the arthroscope and brings debris and blood behind the operator's field of view. The system contains fluid outflow 5 and fluid inflow channels 6. These channels are defined by the space created between the elongated core and the circular sheath surrounding it.

FIG. 2 illustrates a cross-sectional view along Line A-A of FIG. 1. Fluid enters the inflow channels 6 and flows axially into the joints. Fluid exits through the outflow channels 5 and comes behind the distal end of the arthroscopic sheath system and pulls blood and debris behind the field of view of the user. The fluid flow is perpendicular to the system creating a pocket of clear fluid in front of the system where it is needed the most. An elongated core having square radial cross section 7 is inserted into the sheath 2. The inner surface of the sheath 2 can have an extruded profile for mating with the outer surface of the elongated core 7. The outer surface of the elongated core has tabs 8 that mate tightly with the inner surface of the sheath in order to ensure that the elongated core does not rotate within the sheath. The force of the elongated core pushing against the inner surface of the sheath forms a seal between the elongated core 7 and the inner surface of the sheath 2. As shown, fluid inflow 5 channels and fluid outflow channels 6 are created between the outer sheath 2 and the elongated core 7.

Figure 3:
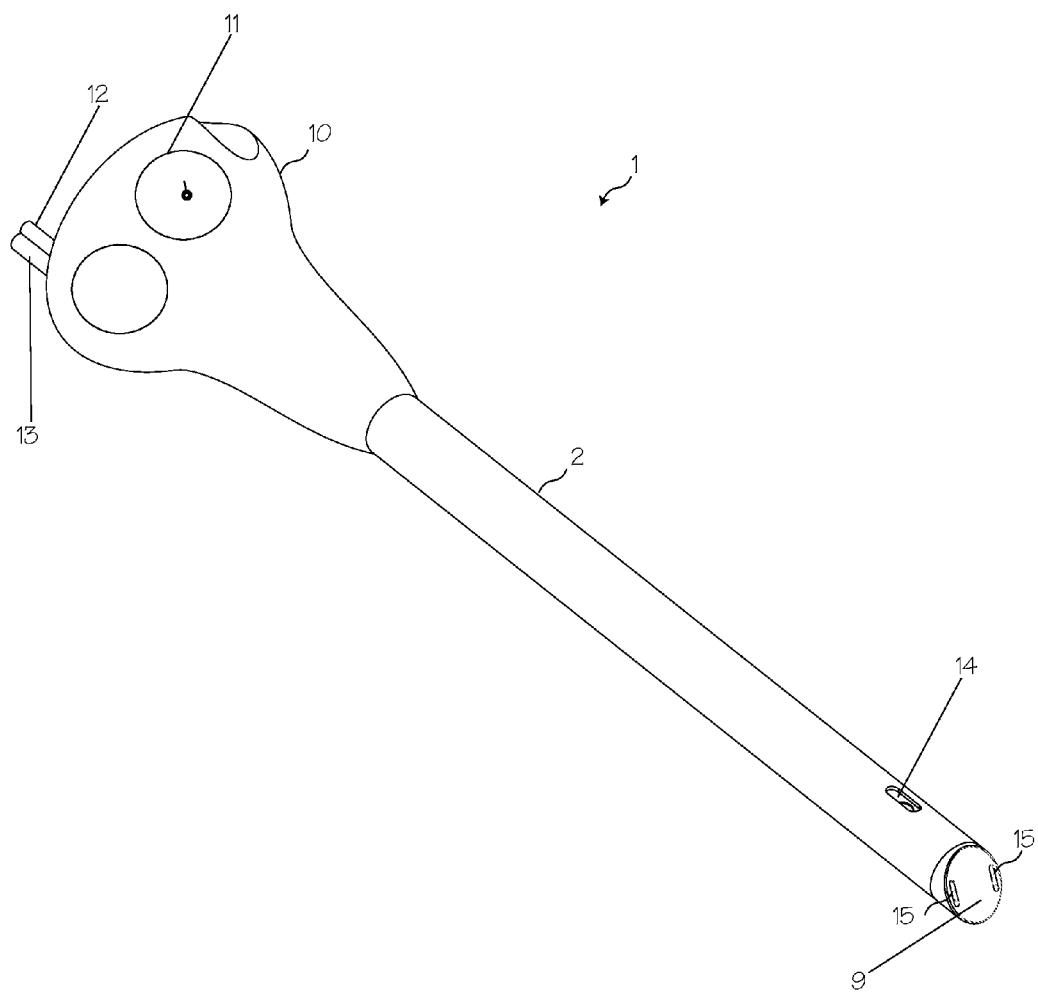
FIG. 3 illustrates an arthroscope having an optical cap.

FIG. 3 illustrates an arthroscope 1 having an optical cap 9. The arthroscope has an ergonomic handle 10 for user comfort. The handle contains user control switches 11 that can provide focusing means for controlling the optical zoom of the system. At the distal end, the arthroscope also contains an electronics cable 12 and fluid inflow and outflow tubing 13. Positioning of the electronics and fluid tubing eliminates clutter of conventional arthroscopes. The optical cap 9 is made of a plastic material and is located at the distal end of the arthroscope. The optical cap 9 may serve as the objective lens if one is not integrated into the imaging chip and associated package. Alternatively, the cap 9 may serve as a protective window, either optically clear or with optical modifying properties such as polarization or color filtering. The arthroscope also contains a fluid drain and sensor window 14. A clear pocket flow of fluid flows axially to the system outflow from the distal end of the system. Drainage flows through openings 15 in the sheath 2. Flow in this direction creates a clear fluid pocket in front of the arthroscope where it is required the most.

Figure 4:
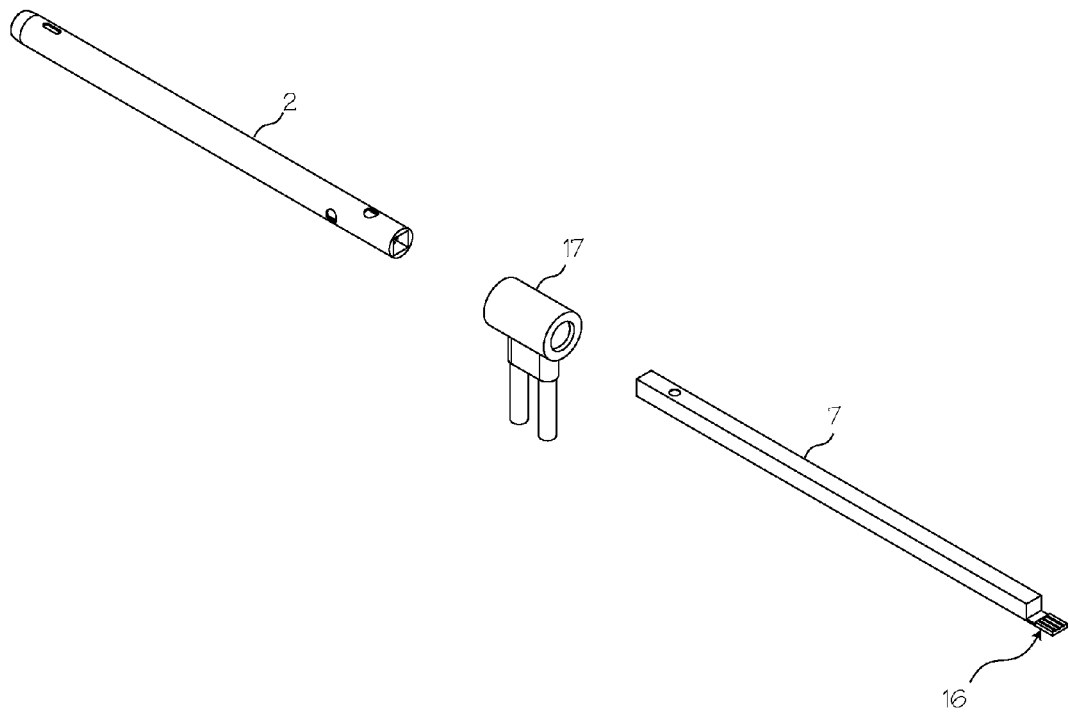
FIG. 4 illustrates the features of the arthroscope pulled apart.

FIG. 4 illustrates the features of the arthroscope 1 pulled apart. The distal end of the elongated core has a multifunction connector 16 for use with the video, pressure and temperature sensors. A round fluid sheath 2 is placed over the elongated core 7 and connected via a hub 17. The hub can be coupled to a multi-channel fluid manifold. The outside diameter of the sheath closely matches the radial cross section of the elongated core to minimize the shape of the arthroscope. When engaged, the inner surface of the external sheath and the outer surface of the elongated core define a plurality of fluid channels extending longitudinally within the arthroscope. The fluid sheath can also have a rectangular radial cross section closely matching the radial cross section of the elongated core.

Figure 5A:
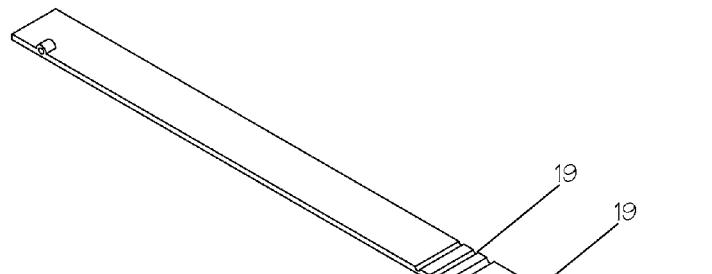
FIGS. 5a and 5b illustrate the elongated core of the arthroscope before it is folded into its final configuration.
Figure 5B:
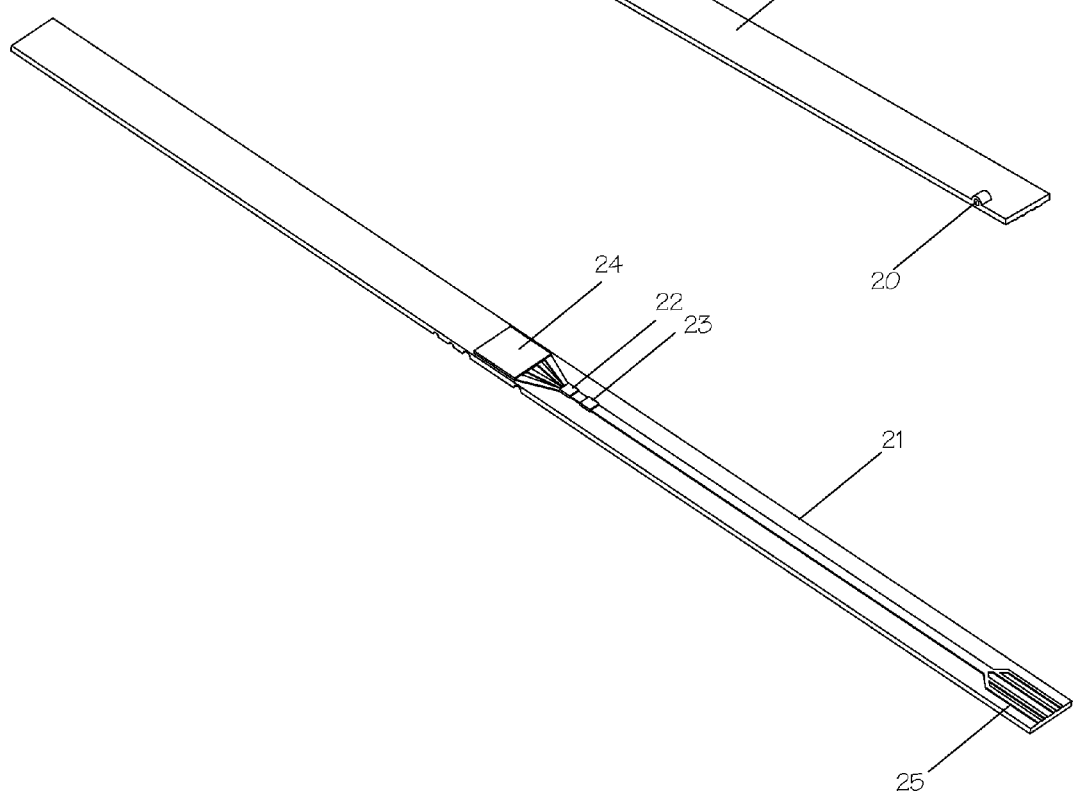

FIGS. 5a and 5b illustrate the elongated core 7 of the arthroscope before it is folded into its final configuration. FIG. 5a illustrates the base of the elongated core. The elongated core is constructed onto a flat molded backing 18. The backing 18 contains folds to create hinge points 19 that allow the backing to fold into the square configuration. The degree to which the folds are rotated allows the angle of the imaging chip to vary according to user preference. Pivot points 20 are contained at each end of the backing for connection of the top and bottom faces of the elongated core. FIG. 5b illustrates the molded backing 18 with a flex circuit 21 laminated onto the molded hinge backing. The flex circuit 21 contains a pressure sensor 22 and a temperature sensor 23 as well as an imaging chip and its sensor module and associated lens 24. The lens can be made of plastic or other similar material to assist in insulating the imaging chip and the inside electronics from damage. In addition, an edge connector 25 is contained on one end of the molded backing for connection to desired system input or power devices.

Figure 6:
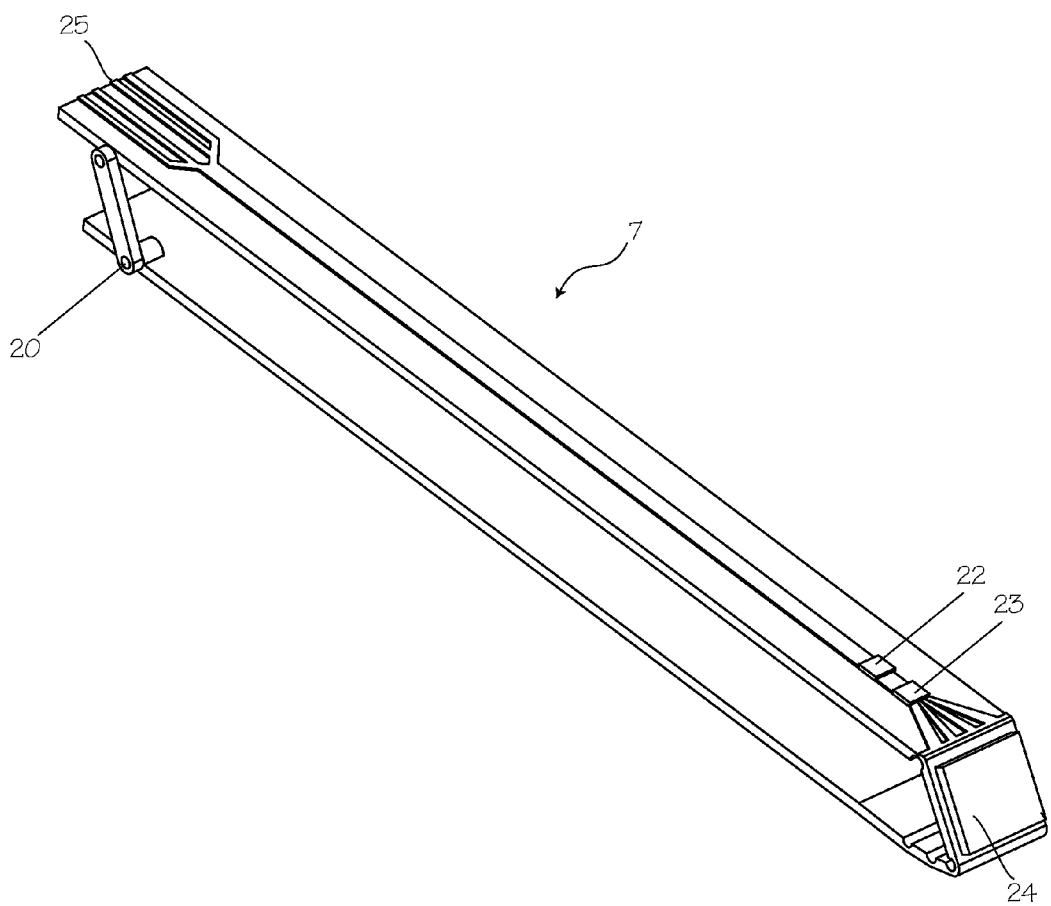
FIG. 6 illustrates the elongated core of the arthroscope in its final folded configuration.

FIG. 6 illustrates the elongated core of the arthroscope in its final folded configuration. At the distal end the elongated core houses the digital image CCD or CMOS chip and a sensor module 24 to enhance image magnification clarity and color. At the proximal end, the elongated core contains a multifunction edge connector 25 for use with the temperature 23 or pressure signal 22 connectors and to carry video signal. This elongated core is open on both sides. The elongated core 7 is formed by folding over the backing 18 and connecting the top and bottom backing faces at the pivot points 20. The elongated core shape is dictated by the combination of the square chip and associated chip package that are of pre-determined sizes and commercially available. The elongated core may contain one or multiple digital image chips within a single arthroscope. Longitudinal movement of a first face of the backing relative to a second face of the backing changes the angle of digital image CCD or CMOS chip to vary relative to the radial plane of the elongated core. The imaging end enables an indefinitely adjustable view angle from 0 degrees to 90 degrees in a single scope. The arthroscope can also accommodate for a 180 degree or retrograde view where the arthroscope has a flat top construction and a rotatable or living hinge rectangular arthroscope architecture. The elongated core 7 can be releasably mounted to a base such that the core can be sterilized and reused for a number of surgical procedures.

FIGS. 7a and 7b illustrate another elongated core 7 before it is folded into its final configuration. FIG. 7a illustrates the backing 18 of the elongated core. The elongated core is constructed onto the molded backing 18 that contains protrusions 26 spaced apart at a predetermined distance. The protrusions on each face are matched to mate when in a folded configuration. When folded, the protrusions construct a solid elongated core. The elongated core has a square radial cross section with a proximal end, a distal end spaced from the proximal end for insertion into a body, a top surface, a bottom surface. The elongated core also has two opposite side surfaces adjacent to the top and bottom surfaces. At least one of the surfaces may contain a metal strip bonded to the top of the surface. The metal strip may be a spring steel or nickel-titanium alloy with a preformed radius of curvature. The metal alloy may alternatively be a malleable metal such as aluminum or may be a nickel-titanium (nitinol) alloy with a shape memory feature. The metal strip allows the elongated core to reliably bend in one plane of curvature. Where the memory backing is spring-steel or nitinol, it may bend to a shape if malleable, or may be made steerable with a nitinol shape-memory component.

The elongated core contains planes that provide structural rigidity to the elongated core. The protrusions can have a locking taper construction. In addition, the protrusions can be joined with an adhesive or can be welded together thermally or with ultrasonic welding techniques. The elongated core also contains an imaging device chip fitted at the distal end of the elongated core where the imaging surface is arranged in a viewing direction of the elongated core. In addition, the elongated core has an illumination source at the proximal end for illuminating a surgical site at which the arthroscopic sheath system is directed. The core backing 18 contains folds that create hinge points 19 to allow the backing to fold into a rectangle. Pivot points 20 are contained at each end of the backing for connection of the top and bottom faces of the elongated core. FIG. 7b illustrates the molded backing 18 with a flex circuit 21 laminated onto the molded hinge backing. The flex circuit 21 contains the pressure and temperature sensors 22, 23 as well as the imaging chip and its associated LED package 24. In addition, the edge connector 25 is contained on one end of the molded backing.

Figure 8:
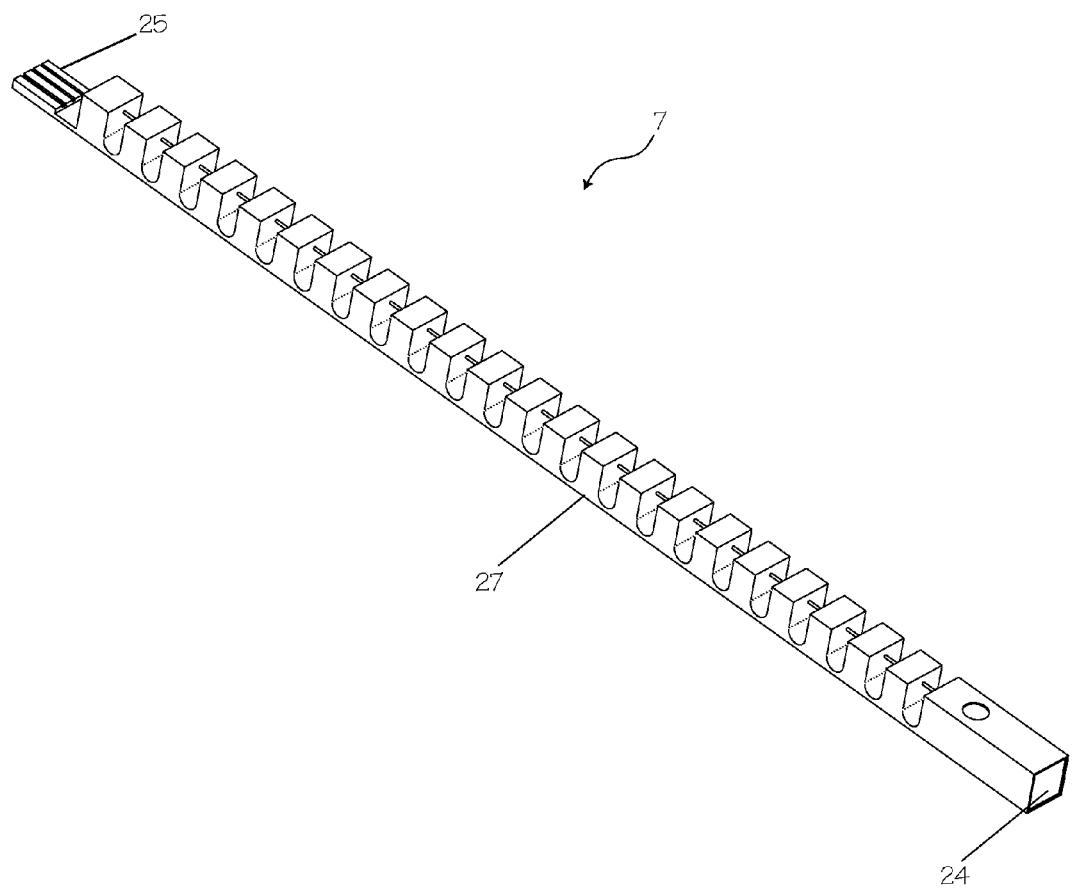
FIG. 8 illustrates another elongated core configuration.

FIG. 8 illustrates another elongated core configuration. The distal end of the elongated core 7 houses the digital image CCD or CMOS chip and sensor module 24. The distal end can also contain imaging modalities other then visible light devices such as ultrasonic transducers and optical coherence tomography (OCT) imagers in addition to the CCD and CMOS video imagers. At the proximal end, the elongated core contains a multifunction edge connector 25 for use with temperature or pressure signal connectors. The intermediate body of the elongated core is in the form of vertebrated or specifically profiled sections 27 located at a predetermined distance from each other to enhance steerability of the elongated core when inserted into the patient. The elongated core is transversely slotted along its entire length to form this configuration.

Figure 9:
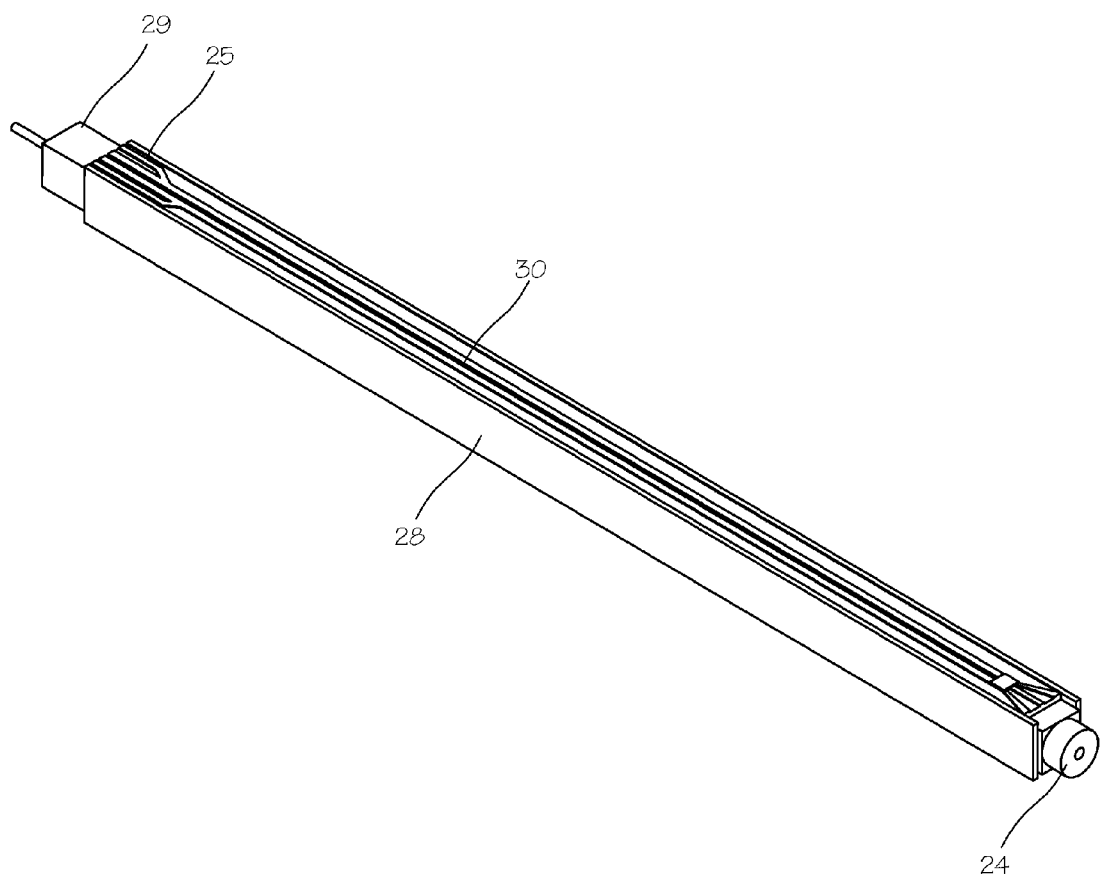
FIG. 9 illustrates an elongated core with a square tube or solid mandrel for additional rigidity.

FIG. 9 illustrates an elongated core with a square tube or solid mandrel for additional rigidity. The rectangular mandrel may serve as an illumination conduit. The assembly has an optically transparent light pipe center core 28 that allows light to pass through. Illumination light emanating from a light source apparatus passes through the transparent core, is converged by a lens, and falls on the opposing end surface of the illumination conduit. The illumination light is transmitted to the arthroscope over the illumination conduit, passes through the arthroscope, and is emitted forward through the distal end of the arthroscope. Thus, an object in the patient's body cavity is illuminated. An image represented by the light reflected from the illuminated object is formed by the arthroscope. A resultant object image is projected by the imaging means through the scope. The optically transmitting center core is a rectangular shaped housing or mandrel made of a molded plastic material that can transmit light from the proximal end and out of the distal end. The center core is made of any clear molded polycarbonate or acrylic plastic material that can be easily molded. The molded plastic mandrel has an LED illumination module 29 at the proximal end and the assembly circuitry 30 is wrapped around the center core. The edge connector 25 is also contained at the proximal end of the assembly. The chip imaging module 24 is contained at the distal end of the assembly. In addition, the distal end of the assembly serves as the transmitting end of the light pipe created by the center core. The advantage to the assembly is that it has a small cross-section, but is very robust and easy to use. The assembly is inexpensive to manufacture and provides adequate illumination to the arthroscope.

Figure 10:
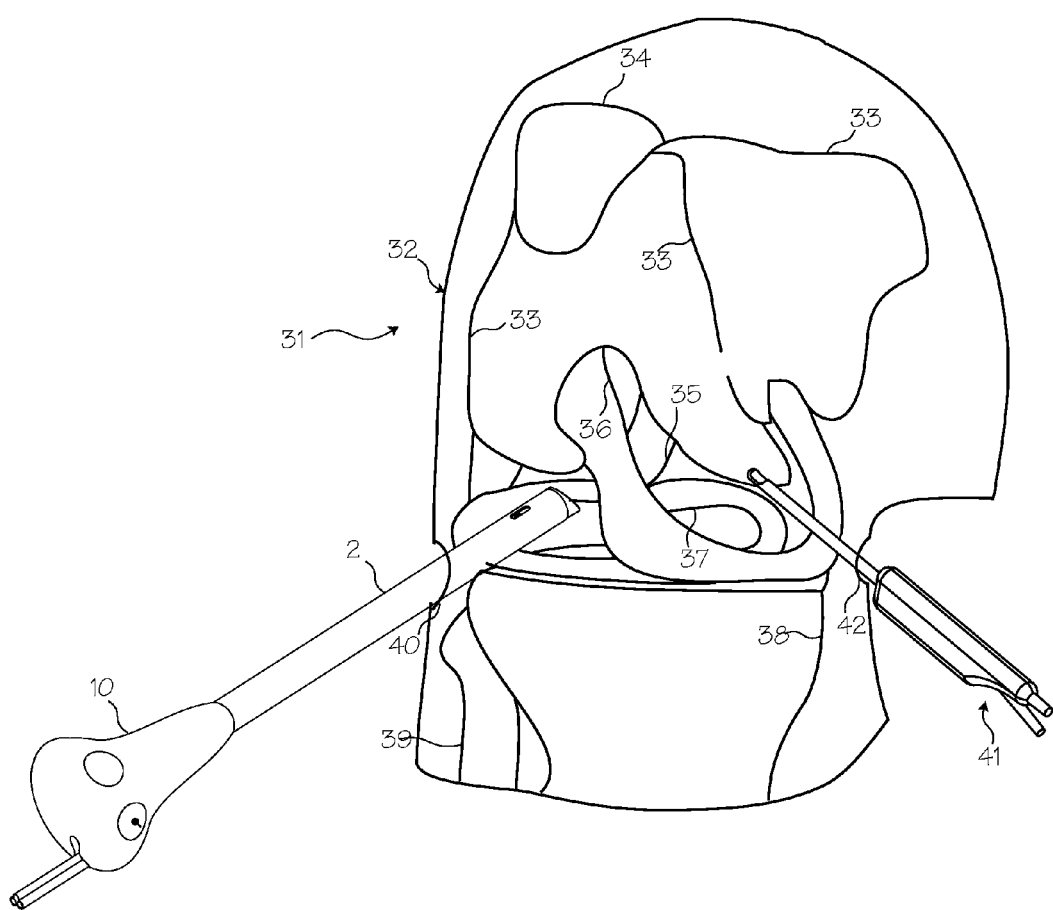
FIG. 10 illustrates a method of performing arthroscopic surgery on a patient using an arthroscope containing an elongated core with a square radial cross section.

FIG. 10 shows a method of performing arthroscopic surgery on a patient 31 using an arthroscope in an atraumatic sheath 2. Various anatomical landmarks in the patient's knee 32 are shown for reference, including the femur 33, patella 34, posterior cruciate ligament 35, anterior cruciate ligament 36, meniscus 37, tibia 38 and fibula 39. During surgery, the surgeon introduces the arthroscope into the knee via a first incision 40 in order to visualize the surgical field. A trimming instrument 41 is introduced through a second incision 42 to remove or trim tissue that the surgeon determines should be removed or trimmed.

Figure 11:
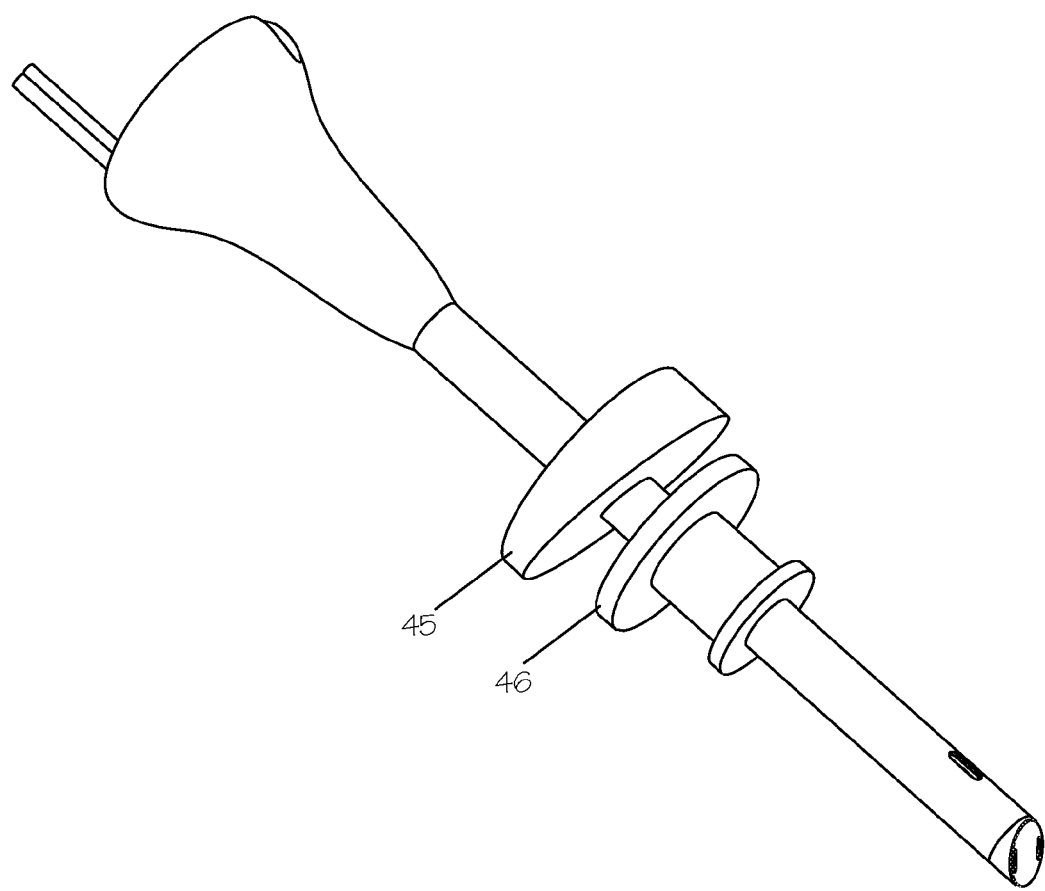
FIG. 11 illustrates an arthroscope where the fluid management is contained in a grommet-type cannula.

FIG. 11 illustrates an arthroscope where the fluid management is contained in a grommet-type cannula. The arthroscope has an angle set collar 45 and an elastomeric portal cannula 46. When the collar is not pressed to the elastomeric cannula, the scope set perpendicular to the portal. When the sleeve is pushed forward, the scope is angled in the portal. Where the collar is rotated, the arthroscope can be directed to an area of interest radially within the surgical space. The ability to translate, rotate and hold the scope can be accomplished with a ball gimbal or other similar means. This frees the hands of the surgeon to use their instruments rather than have to hold the arthroscope in position.

Figure 12:
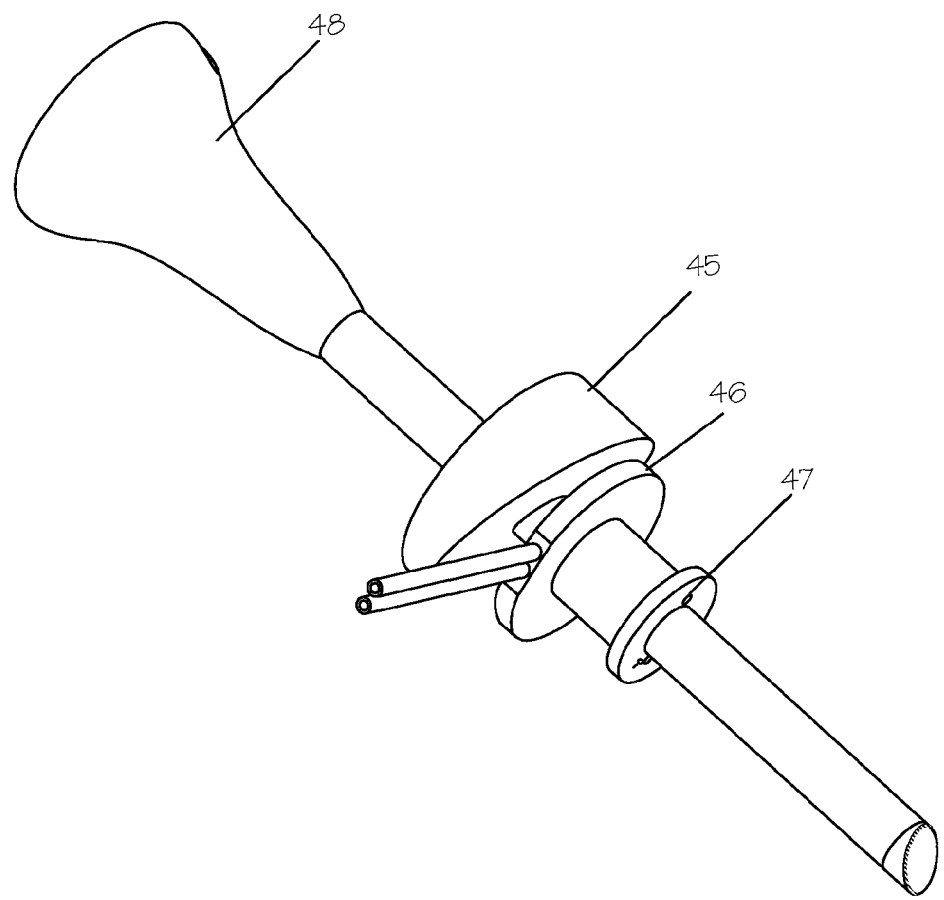
FIG. 12 illustrates an arthroscope that can be used without requiring a user to hold it, providing the user the opportunity to use the arthroscope hands free.

FIG. 12 illustrates an arthroscope that can be used without requiring a user to hold it, providing the user the opportunity to use the arthroscope hands free. The arthroscope has an angle set collar 45, an elastomeric portal cannula 46 and a grommet cannula 47 to allow for fluid inflow and outflow through the grommet cannula. The fluid and gas management connections are removed from the arthroscope. The arthroscope also contains a wireless scope 48 that accommodates for multiple scopes to communicate on a network. This allows the arthroscope to be wireless and untethered by either wires or fluid tubes and instead to be aimed and held on a point of interest. This provides the advantage that the surgeon can use both hands while operating on a patient and can be useful in telemedicine applications. The arthroscope is wireless and can be networked together with a ZigBee, MESH or Bluetooth wireless network.

Figure 13:
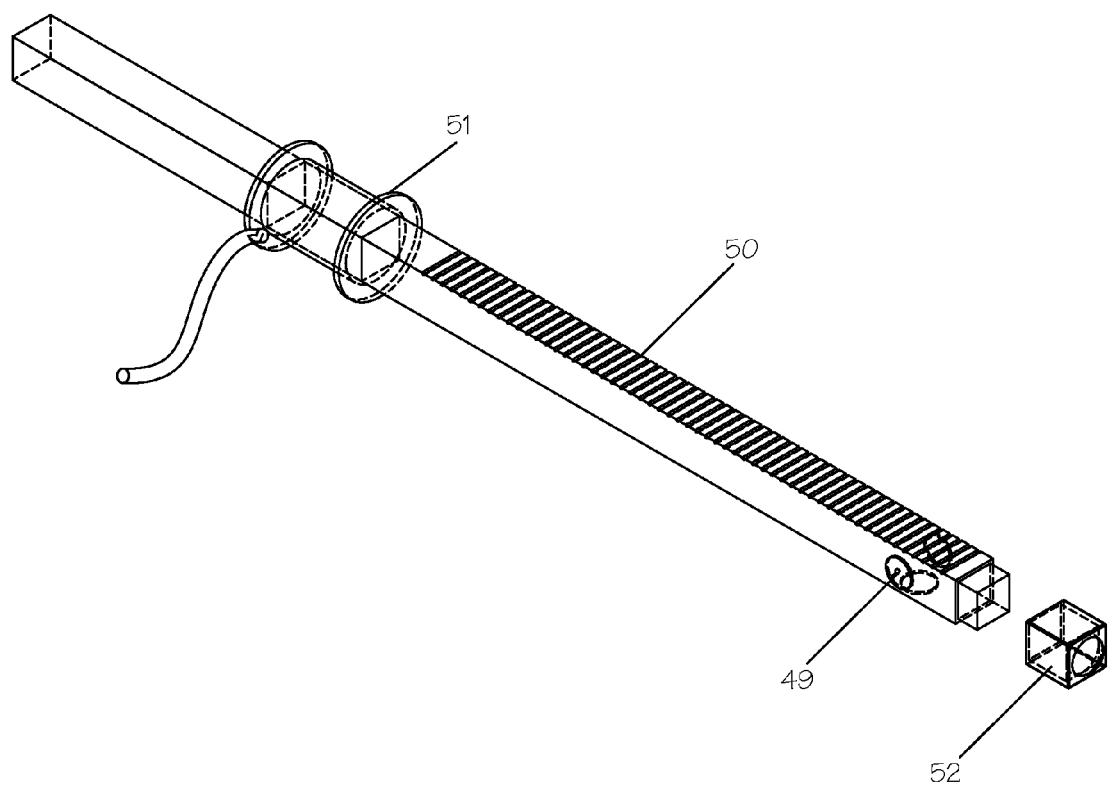
FIG. 13 illustrates an arthroscope with a molded optical cap and 3-D positioning sensors.

FIG. 13 illustrates an arthroscope with a molded optical cap and 3-D positioning sensors. Spatial positioning and tracking sensors 49 can be attached to 3 of the 4 orthogonal sides of the arthroscope. These sensors can read optically, ultrasonically, or with an RFID system. The positioning and tracking system allows the arthroscope to be positioned accurately in space and can be used to guide surgical instruments and provide accurately guided cutting of tissue. In addition, due to the arthroscope's flat surface, a linear encoder 50 can be added to the arthroscope using circuit printing lithography techniques. This can be used to accurately gauge the depth of penetration of the scope into the surgical field. A reader 51 for the linear encoder is disposed within an access cannula. The data from the 3-D positioning and tracking means 49 and linear encoder 50 may be transmitted for display and processing either wired, or wirelessly. The 3-D and linear positioning encoders may be on two or more arthroscopes and can communicate and network together with a ZigBEE MESH network, Bluetooth 802.11 or other wireless protocol. The 3-D positioning and tracking can be useful for robotic surgery, virtual template aided surgery, augmented reality surgical visualization and high-risk surgery, or implant surgery where geometrically accurate cutting is essential to the proper alignment of a device such as an orthopedic implant. The system also has an optical cap 52 to protect the imaging chip from fluids. The cap is molded of acrylic, polycarbonate, or other appropriate optically clear plastic. The cap may be molded with a spherical lens, an aspheric lens, or a split stereoscopic lens that projects a binocular image on to the imaging chip. The central square rod may have a structural center core (e.g. stainless steel or titanium), to give the scope strength, and the perimeter of the rod may be clad with an optically clear light pipe of a light-transmitting plastic. The rod is illuminated at the proximal end with an LED light source or a fiber optic cable, and the light is transmitted through a pipe light, through the optical cap 52 out the distal end to illuminate the surgical field. On the perimeter, the optical cap may have a condensing lens feature, or a light diffusion means to tailor the illumination to the clinical needs of the surgeon. The system may be used with a fluid management sheath and means previously disclosed. Also the ability to build 100% polymer and non-ferrous arthroscope allows its use in radiology guided applications where the materials must be non-magnetic, such as under MRI applications.

In use, a surgeon inserts the elongated core into the sheath of corresponding size. The elongated core creates the most space efficient configuration in that the insertion of the elongated core into the smallest complimentary circular shaped sheath eliminates wasted space. In addition, the arthroscope allows for an efficient clear pocket view flow of fluid inflow and outflow to create a clear field of view for the surgeon. Also, the arthroscope can be used as a retractor once inserted in the patient.

The arthroscope architecture allows the largest possible elongated core to be used in the smallest scope sheath. The elongated core dimensions are matched to the scope sheath to accommodate for a low profile system. Further, the arthroscope allows for a flat rectangular scope with a panoramic view, as well as 3-D viewing where two chips are placed side-by-side. In addition, multiple arthroscopes can be used at the same time in a single application system. Two or more arthroscopes can be aimed at a particular area of interest and the user can switch between the arthroscopic cameras with a selector device such as a footswitch. This frees up the user's hands to focus on other surgical instruments such as an arthroscopic shaver or stitcher without requiring use of his hands to hold the camera in place. The multiple arthroscope configuration can be held in place by a portal plug device. The plug can have an angled foot and be rotated to place the arthroscope at the desired angle. A plug can anchor the surgical portal as well as provide a means for sealing the portal to prevent leakage of fluid or gas. The plug can have a square inner lumen to seal against a square arthroscope that does not have an outer round sheath. The two or more cameras can be switched back and forth to cover multiple locations from a central console. The cameras can be of different focal lengths or have imaging capabilities such as narrow-light band imaging, near infra-red, optical coherence tomography miniature radiology device or other non visible light imaging modalities.

The word arthroscope used herein includes a family of instruments, including endoscopes, laparoscopes and other scopes. The scopes may use rod optics, fiber optics, distally mounted CCD chips, or other optical systems. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of performing arthroscopic surgery, said method comprising the steps of:
   providing an arthroscope having a proximal end and a distal end, said arthroscope comprising:
   a molded elongated core having an inner and outer surface and a square radial cross section and having a proximal end, a distal end spaced from the proximal end for insertion into a body, a top surface with at least one hinge point, and a bottom surface with at least one hinge point, the top and bottom surfaces spaced apart at a predetermined distance;
   an imaging chip fitted at the distal end of the elongated core having an imaging surface arranged in a viewing direction of the arthroscope; and
   a sheath having an outer diameter and an inner diameter, the inner diameter having an extruded profile wherein the inner surface of the sheath and the outer surface of the elongated core define an inflow channel extending longitudinally within the arthroscope and an outflow channel extending longitudinally within the arthroscope in a space defined between the inner surface of the sheath and the outer surface of the elongated core;
   adjusting the top surface of the elongated core via longitudinal movement of the top surface of the elongated core relative to the bottom surface of the elongated core in order to change an angle of the imaging chip relative to a radial plane of the elongated core; and
   performing an arthroscopic surgical procedure.

2. The method of claim 1 further comprising introducing fluid into a body cavity via the inflow channel and then exiting the fluid from the body cavity through the outflow channel disposed proximal of the inflow channel, wherein an opening to the outflow channel is formed within an outer wall of the sheath such that fluid flows perpendicular to a longitudinal axis of the arthroscope to enter the outflow channel from the opening.

3. The method of claim 1 further comprising providing an illumination source at the proximal end of the arthroscope for illuminating a surgical site at which the arthroscope is directed.

4. The method of claim 1 wherein the arthroscope further comprising two opposite side surfaces adjacent to the top and bottom surfaces.

* * * * *